United States Patent
Pan et al.

(10) Patent No.: US 9,072,919 B2
(45) Date of Patent: Jul. 7, 2015

(54) SYNERGISTIC ANTIOXIDANT COSMETIC COMPOSITIONS CONTAINING AT LEAST ONE OF BAICALIN AND TAXIFOLIN, AT LEAST ONE OF CAFFEINE AND NICOTINAMIDE, AT LEAST ONE OF VITAMIN C AND RESVERATROL AND FERULIC ACID

(71) Applicants: Zhi Pan, Fort Lee, NJ (US); Jean-Thierry Simonnet, Mamaroneck, NY (US); Ashleigh Murtaugh, Piscataway, NJ (US); Jamie Iannacone Spomer, Metuchen, NJ (US)

(72) Inventors: Zhi Pan, Fort Lee, NJ (US); Jean-Thierry Simonnet, Mamaroneck, NY (US); Ashleigh Murtaugh, Piscataway, NJ (US); Jamie Iannacone Spomer, Metuchen, NJ (US)

(73) Assignee: L'OREAL S.A., Paris (FR)

( * ) Notice: Subject to any disclaimer, the term of this patent is extended or adjusted under 35 U.S.C. 154(b) by 97 days.

(21) Appl. No.: 13/650,865

(22) Filed: Oct. 12, 2012

(65) Prior Publication Data
US 2014/0107046 A1    Apr. 17, 2014

(51) Int. Cl.
| | | |
|---|---|---|
| A61Q 19/00 | (2006.01) | |
| A61Q 19/08 | (2006.01) | |
| A61K 8/34 | (2006.01) | |
| A61K 8/67 | (2006.01) | |
| A61K 8/36 | (2006.01) | |
| A61K 8/49 | (2006.01) | |
| A61K 8/365 | (2006.01) | |
| A61K 8/60 | (2006.01) | |
| A61K 47/22 | (2006.01) | |
| A61K 47/10 | (2006.01) | |

(52) U.S. Cl.
CPC ............... *A61Q 19/08* (2013.01); *A61K 8/347* (2013.01); *A61K 8/676* (2013.01); *A61K 8/675* (2013.01); *A61K 8/36* (2013.01); *A61K 8/494* (2013.01); *A61K 47/22* (2013.01); *A61K 47/10* (2013.01); *A61K 8/365* (2013.01); *A61K 8/498* (2013.01); *A61K 8/602* (2013.01)

(58) Field of Classification Search
None
See application file for complete search history.

(56) References Cited

U.S. PATENT DOCUMENTS

| | | |
|---|---|---|
| 3,501,409 A | 3/1970 | Matson |
| 3,839,210 A | 10/1974 | Beiswanger et al. |
| 4,680,143 A | 7/1987 | Edge et al. |
| 5,532,012 A | 7/1996 | Balentine et al. |
| 5,686,082 A | 11/1997 | N'Guyen |
| 5,817,299 A * | 10/1998 | Manirazman .................. 424/59 |
| 6,121,209 A | 9/2000 | Watts et al. |
| 6,180,662 B1 * | 1/2001 | Lanzendorfer et al. ....... 514/456 |
| 6,331,520 B1 | 12/2001 | Richardson |
| 6,355,657 B1 | 3/2002 | Osborne |
| 6,423,327 B1 | 7/2002 | Dobson, Jr. et al. |
| 6,479,442 B1 | 11/2002 | Berube et al. |
| 6,645,513 B2 | 11/2003 | Dobson, Jr. et al. |
| 6,646,035 B2 | 11/2003 | Koch et al. |
| 6,733,797 B1 | 5/2004 | Summers |
| 6,949,496 B1 | 9/2005 | Boutique et al. |
| 7,452,549 B2 | 11/2008 | Hasler-Nguyen et al. |
| 2002/0086042 A1 | 7/2002 | Delrieu et al. |
| 2002/0110604 A1 | 8/2002 | Babish et al. |
| 2003/0031715 A1 | 2/2003 | Park et al. |
| 2003/0152536 A1 | 8/2003 | Pauly et al. |
| 2003/0206972 A1 | 11/2003 | Babish et al. |
| 2004/0146474 A1 | 7/2004 | Galey |
| 2005/0158271 A1 | 7/2005 | Lee et al. |
| 2005/0266121 A1 | 12/2005 | Lines et al. |
| 2005/0271608 A1 | 12/2005 | Gupta |
| 2006/0110439 A1 | 5/2006 | Tobia et al. |
| 2007/0208088 A1 | 9/2007 | Lipshutz |
| 2007/0232561 A1 | 10/2007 | Leung et al. |
| 2008/0089941 A1 | 4/2008 | Mower |
| 2008/0095866 A1 | 4/2008 | Declercq et al. |
| 2008/0176956 A1 | 7/2008 | Hsu |
| 2008/0219927 A1 | 9/2008 | Thakur et al. |
| 2008/0319015 A1 | 12/2008 | Gruenewald et al. |
| 2009/0110674 A1 | 4/2009 | Loizou |
| 2009/0131340 A1 | 5/2009 | Lanzendorfer et al. |
| 2009/0233876 A1 | 9/2009 | Auriol et al. |
| 2010/0047297 A1 | 2/2010 | Petersen |
| 2010/0166851 A1 * | 7/2010 | Dallas ........................... 424/451 |
| 2010/0255079 A1 | 10/2010 | Sanmiguel et al. |
| 2011/0033525 A1 | 2/2011 | Liu |
| 2011/0067294 A1 | 3/2011 | Ng et al. |
| 2011/0136245 A1 | 6/2011 | Parker |
| 2011/0152214 A1 | 6/2011 | Boison et al. |
| 2012/0071550 A1 | 3/2012 | Zelkha et al. |

FOREIGN PATENT DOCUMENTS

| | | | | |
|---|---|---|---|---|
| CN | 102579820 A | * | 7/2012 | ........... A61K 36/898 |
| JP | 2005200334 A | * | 7/2005 | ............. A61K 35/78 |
| WO | WO-2006024545 A1 | | 3/2006 | |

(Continued)

OTHER PUBLICATIONS

Gattuso, G., Barreca, D., Gargiulli, C., Leuzzi, U., & Caristi, C. (2007). Flavonoid composition of citrus juices. Molecules, 12(8), 1641-1673.*

(Continued)

*Primary Examiner* — Shaojia Anna Jiang
*Assistant Examiner* — Dale R Miller
(74) *Attorney, Agent, or Firm* — Novak Druce Connolly Bove + Quigg LLP

(57) ABSTRACT

The invention provides synergistic aqueous compositions comprising at least one flavonoid, and ferulic acid, and optionally one or more additional antioxidants, for cosmetic use.

6 Claims, 1 Drawing Sheet

(56) References Cited

FOREIGN PATENT DOCUMENTS

| WO | WO-2012103637 A1 | 8/2012 |
| WO | WO-2013016257 A1 | 1/2013 |

OTHER PUBLICATIONS

Tapas, A. R., Sakarkar, D. M., & Kakde, R. B. (2008). Flavonoids as nutraceuticals: a review. Tropical Journal of Pharmaceutical Research, 7(3), 1089-1099.*

Suzuki, H. et al., "Mechanistic Studies on Hydrotropic Solubilization of Nifedipine in Nicotinamide Solution." *Chem. Pharm. Bull.* 46(1), 125-130 (1998).

Evstigneev, M.P. et al., "Effect of a mixture of caffeine and nicotinamide on the solubility of vitamin (B2) in aqueous solution," *European Journal of Pharmaceutical Sciences* 28, 59-66 (2006).

Da Silva, R.C. et al., "Investigations on the mechanism of aqueous solubility increase caused by some hydrotropes." *Thermochimica Acta* 328, 161-167 (1999).

Huh, K.M. et al., "A new hydrotropic block copolymer micelle system for aqueous solubililzation of paclitaxel." *Journal of Controlled Release* 126, 122-129 (2008).

Takahashi, K. et al., "Application of hydrotropy to transdermal formulations: hydrotropic solubilization of polyol fatty acid monoesters in water and enchancement effect on skin permeation of 5-FU." *Journal of Pharmacy and Pharmacology* 63, 1008-1014 (2011).

Nicoli, S. et al., "Association of nicotinamide with parabens: Effect on solubility, partition and transdermal permeation." *European Journal of Pharmaceutics and Biopharmaceutics* 69, 613-621 (2008).

Nidhi, K. et al., "Hydrotropy: A Promising Tool for Solubility Enhancement: A Review." *International Journal of Drug Development & Research* 3(2), 26-33 (2011).

Notification of Transmittal of the International Search Report and the Written Opinion of the International Searching Authority, or the Declaration; International Search Report; Written Opinion of the International Searching Authority, International Application No. PCT/US2013/064461.

* cited by examiner

SYNERGISTIC ANTIOXIDANT COSMETIC COMPOSITIONS CONTAINING AT LEAST ONE OF BAICALIN AND TAXIFOLIN, AT LEAST ONE OF CAFFEINE AND NICOTINAMIDE, AT LEAST ONE OF VITAMIN C AND RESVERATROL AND FERULIC ACID

FIELD OF THE INVENTION

The present invention relates to aqueous compositions comprising at least one flavonoid, and ferulic acid, and optionally one or more additional antioxidants, for cosmetic use.

BACKGROUND OF THE INVENTION

The formation of free radicals is a widely accepted pivotal mechanism leading to skin aging. Free radicals are highly reactive molecules with unpaired electrons that can directly damage various cellular membranes, lipids, proteins, RNA and DNA. The damaging effects of these reactive oxygen species are induced internally during normal metabolism and externally through various oxidative stresses. UV exposure and environmental pollution can accelerate skin aging by producing free radicals in skin.

Antioxidants protect cells from the damage of oxidative stress by scavenging free radicals and inhibiting following oxidation reactions. The topical application of antioxidants is broadly used in skin care product to prevent skin aging.

Previously, in cosmetic related fields, polyphenols were reported to show synergistic effects with other antioxidants such as Vitamin E or carotenoids. Also synergistic antioxidant effects were reported based on the combination of carotenoids and tocotrienols.

U.S. Pat. No. 7,452,549, Nestec S. A., discloses a synergistic antioxidant combination of delta tocols and polyphenols. U.S. application publication 2012/0071550, Lycored Ltd., discloses Synergistic combinations of carotenoids and polyphenols. U.S. Pat. No. 5,686,082, L'Oreal, discloses cosmetic or pharmaceutical compositions containing a combination of a polyphenol and a ginkgo extract. U.S. application publication 2003/0206972, J. G. Babish and T. Howell, discloses compositions containing carotenoids and tocotrienols and having synergistic antioxidant effects.

U.S. Pat. No. 7,452,549 measured NO, TNF, PGE2, superoxide inhibition and showed the synergistic effects between delta tocols and polyphenols on suppression of low density lipoprotein oxidation in serum. U.S. application publication 2012/0071550 used UV absorbance and showed synergistic combinations of polyphenols and carotenoids, which can be used to inhibit the production of various inflammatory mediators. None of these patents teach the synergistic effect between phenolic compounds themselves.

In other fields, synergistic antioxidant associations are used to improve the oxidative stability of other chemical in the same systems, such as lubricating oil, biodiesel fuel, and other thermoplastic polymers. U.S. Pat. No. 6,121,209, Exxon, discloses a synergistic antioxidant system. U.S. application publication 2011/0067294, K. Y. S. Ng et al., discloses the effect of natural and synthetic antioxidants on the oxidative stability of biodiesel. U.S. Pat. No. 6,646,035, Clariant Finance (BVI) Limited, discloses synergistic combinations of phenolic antioxidants. U.S. Pat. No. 3,839,210, GAF Corporation, discloses antioxidant compositions comprising a synergistic mixture of a phenol, amice and sulfone.

Combinations of antioxidants are also known in the fields of nutritional supplements, food and beverages. U.S. application publication 2011/0136245, T. L. Parker, discloses synergistic interactions of phenolic compounds found in food. U.S. application publication 2005/0266121, T. C. Lines et al., discloses antioxidative compositions. U.S. application publication 2009/0110674, N. C. Loizou, discloses health supplements. U.S. Pat. No. 6,733,797, W. K. Summers, discloses neuroceuticals for improving memory and cognitive abilities. U.S. application publication 2002/0110604, Ashni Naturaceutical, Inc., discloses compositions exhibiting synergistic antioxidant activity. In these patents, certain phenolic combinations with specific ratios occurring in natural foodstuffs have been reported in U.S. application publication 2011/0136245 only for human nutritional or food preservation; certain phenolic antioxidant combinations have been reported in U.S. Pat. No. 6,646,035 as a stabilizer composition for thermoplastic polymers which are not applicable for cosmetics. None of these patents teach the synergistic effects between phenol/polyphenol compounds that are used in cosmetic formulations.

BRIEF SUMMARY OF THE INVENTION

The invention provides aqueous compositions comprising (a) at least one flavonoid and (b) ferulic acid, wherein the flavonoid (a), and ferulic acid (b) are present in the compositions in amounts sufficient to produce synergistic antioxidant activity.

The compositions can also contain additional antioxidants. The invention thus also provides aqueous compositions comprising aqueous compositions comprising (a) at least one flavonoid, (b) ferulic acid, and (c) one or more additional antioxidants different than (a) and (b), wherein the flavonoid (a), ferulic acid (b) and antioxidant (c) are present in the compositions in amounts sufficient to produce synergistic antioxidant activity.

Exemplary flavonoids include baicalin and taxifolin. Exemplary additional antioxidants (c) include vitamin C and resveratrol.

The compositions can optionally contain at least one hydrotrope, such as caffeine or nicotinamide that is acceptable for use in cosmetic compositions, and/or at least one glycol.

Another aspect of the invention provides methods for preparing an aqueous composition comprising including in the composition (a) at least one flavonoid and (b) ferulic acid in amounts sufficient to produce synergistic antioxidant activity. For compositions additionally comprising (c) one or more additional antioxidant different than (a) and (b), the methods for preparing an aqueous composition comprise including in the composition (a) at least one flavonoid, (b) ferulic acid, and (c) one or more additional antioxidants different than (a) and (b), wherein the flavonoid (a), ferulic acid (b) and antioxidant (c) are present in amounts sufficient to produce synergistic antioxidant activity.

A further aspect of the invention provides methods comprising applying an aqueous composition to skin, the aqueous composition comprising (a) at least one flavonoid and (b) ferulic acid in amounts sufficient to produce synergistic antioxidant activity. For compositions additionally comprising (c) one or more additional antioxidants different than (a) and (b), the methods comprise applying an aqueous composition to skin, the aqueous composition comprising (a) at least one flavonoid, (b) ferulic acid, and (c) one or more additional antioxidants different than (a) and (b), wherein the flavonoid (a), ferulic acid (b) and antioxidant (c) are present in amounts sufficient to produce synergistic antioxidant activity.

These and other aspects of the invention are set out in the appended claims, and described in greater detail in the detailed description of the invention.

DETAILED DESCRIPTION OF THE INVENTION

Figure 1:
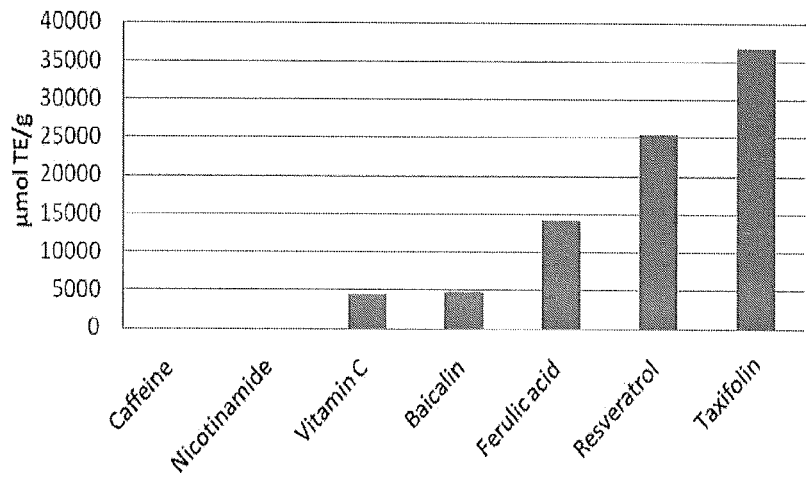
FIG. 1 shows a graph of ORAC results of individual compounds.

The present invention provides aqueous compositions comprising (a) at least one flavonoid and (b) ferulic acid, wherein the flavonoid (a) and ferulic acid (b) are present in amounts sufficient to produce synergistic antioxidant activity. The compositions can also contain additional antioxidants. The invention thus also provides aqueous compositions comprising aqueous compositions comprising (a) at least one flavonoid, (b) ferulic acid, and (c) one or more one additional antioxidant different than (a) and (b), wherein the flavonoid (a), ferulic acid (b) and antioxidant (c) are present in amounts sufficient to produce synergistic antioxidant activity.

The compositions provide stronger protection effects against free radicals and the damaging effects of these reactive oxygen species.

Applicants surprisingly found that the antioxidant capacities of certain phenolic associations, with or without Vitamin C, are dramatically stronger than the additive effects of individual compounds. Strong synergistic effects were observed between at least one flavonoid and ferulic acid, with Vitamin C or resveratrol, which can be applied in cosmetic compositions.

Synergism was determined by comparing the antioxidant capacities of combinations of components measured by oxygen radical absorbance capacity assay (ORAC) with expected or additive values of the individual compounds. The expected ORAC is the combined antioxidant capacity of each individual antioxidant compound in the association, measured individually and assuming that each is functioning independently. The expected ORAC value of a certain association can be calculated by using the following equation:

ORAC(total)=sum of ORAC(compound n, individually)×Percentage(compound n, of use in a cosmetic composition), n=1, 2, 3 . . . .

Synergistic antioxidant activity is present when a measured ORAC is significantly larger than the expected value. Significantly larger than the expected value refers to measured ORAC values at least 25% greater than expected values. Some of the aqueous compositions as shown in the examples exhibit synergistic antioxidant activity greater than 50%.

Oxygen Radical Absorbance Capacity (ORAC) assay is one of most commonly used methods to evaluate the capacity of antioxidants against ROS (reactive oxygen species), specific for peroxyl which is one of the most important free radicals present in the human skin environment.

The ORAC assay measures the oxidative degradation of the fluorescent probe (fluorescein) after being mixed with free radical generators such as azo-initiator compounds (2,2'-Azobis(2-amidinopropane)dihydrochloride, AAPH). Azo-initiators are considered to produce the peroxyl radical by heating, which damages the fluorescent molecule, resulting in the loss of fluorescence. Antioxidants are considered to protect the fluorescent molecule from the oxidative degeneration. By quantifying the decay of fluorescence using a fluorometer, the degree of protection is determined comparing with a standard control antioxidant Trolox. The result is expressed in μMol equivalent of Trolox. Equipment that can automatically measure and calculate the capacity is commercially available, such as the VarioSkan flash microplate reader from Thermo Scientific.

References disclosing ORAC assays include: Cao G, Alessio H, Cutler R (1993). "Oxygen-radical absorbance capacity assay for antioxidants". Free Radic Biol Med 14 (3): 303-11; Ou B, Hampsch-Woodill M, Prior R (2001). "Development and validation of an improved oxygen radical absorbance capacity assay using fluorescein as the fluorescent probe". J Agric Food Chem 49 (10): 4619-26; Huang D, Ou B, Prior R (2005). "The chemistry behind antioxidant capacity assays". J. Agric. Food Chem. 53 (6): 1841-56; and Garrett A R, Murray B K, Robison R A, O'Neill K L (2010). "Measuring antioxidant capacity using the ORAC and TOSC assays". Advanced Protocols in Oxidative Stress II: Methods in Molecular Biology (series), Donald J Armstrong (ed) 594: 251-62.

The flavonoid, ferulic acid, and additional antioxidant components are present in the compositions in amounts sufficient to produce synergistic antioxidant activity. Synergistic antioxidant activity can be determined using the ORAC assay.

Flavonoids are a specific group of polyphenols. Flavonoids are the most plentiful group of polyphenol compounds. They are further categorized, according to chemical structure, into chalcones, flavones, flavanones, flavanols, flavonols, dihydroflavonols, isoflavonoids, neoflavonoids, catechins, anthocyanidins, and tannins. Over 4,000 flavonoids have been identified, many of which occur in fruits, vegetables and beverages (tea, coffee, beer, wine and fruit drinks). Flavonoids have been reported to have antiviral, anti-allergic, antiplatelet, anti-inflammatory, antitumor and antioxidant activities. Flavonoids protect lipids and vital cell components from damaging oxidative stress by efficiently scavenging free radicals.

Baicalin, a component of Chinese medicinal herb Huang-chin, is a flavone, a type of flavonoid. It is a potent antioxidant that demonstrates potent effects against oxidative stress diseases, inflammation, allergy, cancer, bacterial infections, etc.

Ferulic acid is a hydroxycinnamic acid, which can be broadly found in giant fennel, the seeds of coffee, apple, artichoke, peanut, and orange, as well as in both seeds and cell walls of commelinid plants (such as rice, wheat, oats, and pineapple). Like many natural phenols, it is a strong antioxidant that is very reactive toward free radicals and reduces oxidative stress. Many studies suggest that ferulic acid may have antitumor activity.

The amount of flavonoid or flavonoids present in the aqueous compositions can range from about 0.01% to about 20%; about 0.1% to about 20%; or about 0.1% to about 10%, based on the total weight of the composition.

The amount of ferulic acid present in the aqueous compositions can range from about 0.01% to about 20%; about 0.1% to about 20%; or about 0.1% to about 10%, based on the total weight of the composition.

The compositions can also contain one or more additional antioxidants that is/are different from the flavonoid(s) used in the composition and ferulic acid. Additional antioxidants can be any antioxidant suitable for use in cosmetic formulations. Suitable antioxidants include, but are not limited to, vitamin C, resveratrol, tannic acid, polyphenols, amino acids and derivatives thereof, imidazoles, peptides such as carnosine and derivatives, carotenoids, carotenes (such as α-carotene, β-carotene, and lycopene), α-hydroxy acids (such as citric acid, lactic acid, or malic acid), tocopherols and derivatives (such as vitamin E), vitamin A, co-enzyme Q10, bioflavonoids, glutathione, plant extracts (such as rosemary extract, olive leaf extracts), and green tea extracts. The amount of additional antioxidant present in the aqueous compositions can range from about 0.01% to about 20%; about 0.1% to about 20%; or about 0.1% to about 10%, based on the total weight of the composition.

Some antioxidant compounds, such as phenols/polyphenols, have very low solubility in water. The aqueous compositions can optionally contain at least one hydrotrope or at least one glycol to increase solubility of the antioxidants in water.

Hydrotropes (or hydrotropic agents) are a diverse class of water-soluble compounds that characterized by an amphiphilic molecular structure and ability to dramatically increase the solubility of poorly soluble organic molecules in water. The amount of hydrotrope present in the aqueous compositions can range from about 0.1% to about 20%; about 0.1% to about 10%; or about 1% to about 50%, based on the total weight of the composition.

Most hydrotropes have aromatic structure with an ionic moiety, while some of them are linear alkyl chains, as listed in the table below. Although hydrotropes noticeably resemble surfactants and have the ability to reduce surface tension, their small hydrophobic units and relatively shorter alkyl chain distinguish them as a separate class of amphiphiles. Consequently their hydrophobicity is not sufficient enough to create well organized self-associated structures, such as micelles, even with a high concentration.

Common hydrotropic molecules include: sodium 1,3-benzenedisulfonate, sodium benzoate, sodium 4-pyridinecarboxylate, sodium salicylate, sodium benzene sulfonate, caffeine, sodium p-toluene sulfonate, sodium butyl monoglycolsulfate, 4-aminobenzoic acid HCl, sodium cumene sulfonate, N,N-diethylnicotinamide, N-picolylnicotinamide, N-allylnicotinamide, 2-methacryloyloxyethyl phosphorylcholine, resorcinol, butylurea, pyrogallol, N-picolylacetamide 3.5, procaine HCl, proline HCl, nicotinamide, pyridine, 3-picolylamine, sodium ibuprofen, sodium xylenesulfonate, ethyl carbamate, pyridoxal hydrochloride, sodium benzoate, 2-pyrrolidone, ethylurea, N,N-dimethylacetamide, N-methylacetamide, and isoniazid. Hydrotropes can be found in Lee J. et al., "Hydrotropic Solubilization of Paclitaxel: Analysis of Chemical Structures for Hydrotropic Property", Pharmaceutical Research, Vol. 20, No. 7, 2003; and Lee S. et al., "Hydrotropic Polymers: Synthesis and Characterization of Polymers Containing Picolylnicotinamide Moieties", Macromolecules, 36, 2248-2255, 2003.

Cosmetically acceptable hydrotropes refers to hydrotropes that can be used in cosmetic compositions. While hydrotropes represent a broad class of molecules used in various fields, cosmetic applications will be limited due to safety and tolerance restrictions. Suitable hydrotropes for use in cosmetics include, but are not limited to, nicotinamide (vitamin B3), caffeine, sodium PCA (sodium salt of pyrrolidone carbonic acid), sodium salicylate, urea, and hydroxyethyl urea.

The aqueous compositions can also comprise at least one additive conventionally used in the cosmetics field which does not affect the properties of the compositions according to the invention, such as thickeners, fragrances, pearlescent agents, preservatives, sunscreens, anionic or nonionic or cationic or amphoteric polymers, proteins, protein hydrolysates, fatty acids, such as 18-methyleicosanoic acid, vitamins, panthenol, silicones, vegetable, animal, mineral or synthetic oils, gelling agents, antioxidants, solvents, fragrances, fillers, screening agents, odor absorbers and coloring materials. These additives can be present in the composition according to the invention in proportions which are not limited, but which advantageously fall in the range from 0 to 50% by weight, or 1 to 50% by weight, with respect to the total weight of the composition.

The aqueous compositions comprise from about 1 to about 99.9% by weight of water, with respect to the total weight of the composition. The amount of water in the composition can range from about 1 to 99.5%; about 1 to 60%; or about 1 to 50%, based on the total weight of the composition.

The pH of the aqueous compositions is not limited but is generally between 2 and 12, or between 3 and 9. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

Generally, any composition of the invention can be ingested, injected or topically applied to the skin (over any cutaneous region of the body) or to the mucous membranes (oral, jugal, gingival, genital, conjunctival, and the like). Depending on the method of administration under consideration, the composition can be provided in any dosage form normally used.

For topical application to the skin, the composition can have the form in particular of aqueous or oily solutions or of dispersions of the lotion or serum type, of emulsions with a liquid or semi-liquid consistency of the milk type, obtained by dispersion of a fatty phase in an aqueous phase (O/W) or vice versa (W/O), or of suspensions or emulsions with a soft consistency of the aqueous or anhydrous gel or cream type, or else of microcapsules or microparticles, or of vesicular dispersions of ionic and/or nonionic type or of foams. These compositions are prepared according to the usual methods.

For injection, the composition can be provided in the form of aqueous or oily lotions or in the form of serums. For the eyes, the composition can be provided in the form of drops and, for ingestion, it can be provided in the form of capsules, granules, syrups or tablets.

The amounts of the various constituents of the compositions according to the invention are those conventionally used in the fields under consideration.

In the cosmetics field, these compositions constitute in particular creams for cleaning, protecting, treating or caring for the face, for the hands, for the feet, for the major anatomical folds or for the body (for example, day creams, night creams, make-up-removing creams, foundation creams or sun creams), liquid foundations, make-up-removing milks, protective or care body milks, sun milks, lotions, gels or foams for caring for the skin, such as cleansing lotions, sun lotions, artificial tanning lotions, bath compositions, deodorizing compositions comprising a bactericidal agent, aftershave gels or lotions, depilatory creams, compositions for countering insect stings or bites, pain-relieving compositions or compositions for treating certain skin diseases, such as eczema, rosacea, psoriasis, lichen and severe pruritus.

Another aspect of the invention provides a method for preparing the aqueous compositions comprising including in the composition at least one flavonoid; ferulic acid; and at least one additional antioxidant different than (a) and (b), wherein flavonoid (a), ferulic acid (b) and antioxidant (c) are present in amounts sufficient to produce synergistic antioxidant activity. The compositions can be prepared by mixing the components in water using methods known in the art.

Hydrotropes or glycols can be used to increase solubility of the components of the aqueous compositions if solubility of any of components in water is low. A hydrotrope solution is prepared by completely dissolving one or more hydrotropic agents into water. The component(s) are then added in and mixed using stirring bar or any other mixer. Solubilization of the components occurs within minutes, and mixing continued until clear stable solution is obtained, usually within one hour of mixing. No heat is necessary by following this procedure to dissolve phenolic compounds. Everything is prepared at room temperature to keep the stability of phenolic compounds. This is extremely useful to protect the activity of certain compounds and also makes the process much easier.

EXAMPLES

Example 1

To test samples by using ORAC, compounds are dissolved into water-based NaH2PO4 buffer. Therefore, usually only hydrophilic compounds can be tested in this assay. Although the required concentration is very low in the assay and certain organic solvents such as ethanol or acetone can be used to help solubilization, there is still some issue for certain compounds with very limited solubility. Here, by using hydrotropes, clear water-based solutions could be prepared for antioxidant associations. These solutions were used to test the ORAC of different associations. The hydrotropes used, caffeine and nicotinamide, have been tested both individually and in solution to make sure that they have no influence on the capacity of antioxidant compounds.

All the antioxidants selected for association design show potent capacity in ORAC assay, while hydrotropes which just been used to increase the solubility of certain antioxidants have no capacity by themselves. The results of individual compounds are shown in FIG. 1.

Figure 2:
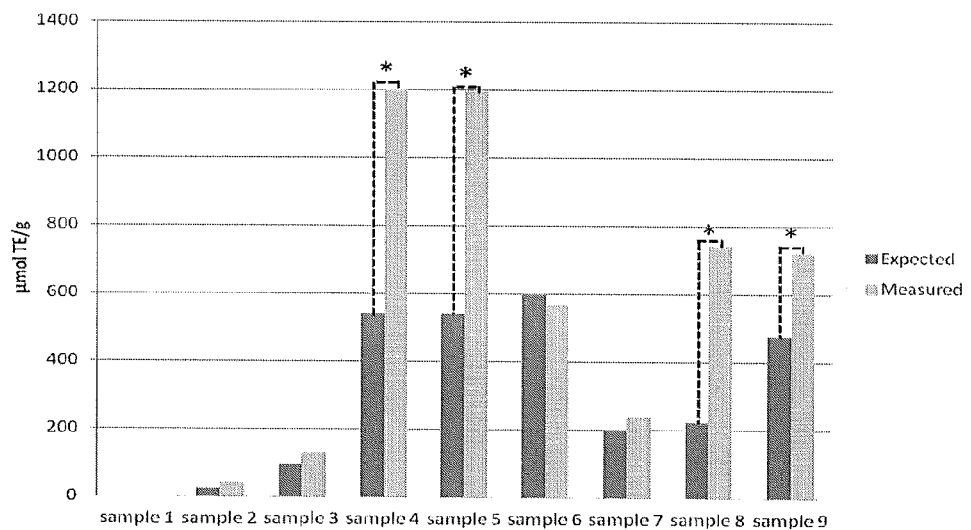
FIG. 2 shows a graph of ORAC results of antioxidant associations compared with expected values. An asterisk (*) shows significant difference between expected and measured values of >50%.

The solubility of baicalin and ferulic acid is very low in water. By using either hydrotropes (5% caffeine, or 5% caffeine and 5% nicotinamide) or organic solvents such as glycols and alcohol, we can co-formulate both of them together with or without a third antioxidant such as resveratrol or Vitamin C in a water-based solution. The antioxidant capacities of different associations were determined by ORAC and compared with their expected ORAC values which are the additive of each individual compounds in the tested formulas. Detailed compositions and tested results are shown in Table 1 and FIG. 2.

TABLE 1

Compositions of tested solution samples.

| Sample number | Composition |
| --- | --- |
| 1 | Control: 5% caffeine and 5% nicotinamide in water |
| 2 | 0.5% baicalin + 5% caffeine and 5% nicotinamide in water |
| 3 | 0.5% baicalin, 0.5% ferulic acid + 5% caffeine and 5% nicotinamide in water |
| 4 | 0.5% baicalin, 0.5% ferulic acid, 10% Vit C + 5% caffeine and 5% nicotinamide in water and glycols |
| 5 | 0.5% baicalin, 0.5% ferulic acid, 10% Vit C + 5% caffeine in water and glycols |
| 6 | 0.5% baicalin, 0.5% resveratrol, 10% Vit C + 5% caffeine in water and glycols |
| 7 | 0.5% resveratrol, 0.5% ferulic acid + 5% caffeine and 5% nicotinamide in water and glycols |

TABLE 1-continued

Compositions of tested solution samples.

| Sample number | Composition |
| --- | --- |
| 8 | 0.5% baicalin, 0.5% ferulic acid, 0.5% resveratrol, + 5% caffeine and 5% nicotinamide in water and glycols |
| 9 | 0.75% taxifolin, 0.5% ferulic acid, 0.5% resveratrol, + 5% caffeine and 5% nicotinamide in water and glycols |

Vit C refers to vitamin C.

Strong synergistic effects only occurred when baicalin and ferulic acid were coformulated with a third antioxidant such as Vitamin C or resveratrol as shown in sample 4, 5 and 8. The synergistic effect is not that obvious without a third antioxidant as shown in sample 3. Such synergy didn't appear when either baicalin or ferulic acid were removed from the association as shown in sample 6 and 7. When another flavonoid compound, taxifolin, replaced baicalin, a strong synergy was also observed as shown in sample 9.

Since these tests were performed on water-based solutions, identified association here are ready to be applied in any cosmetic product to provide a stronger protection from free radicals.

Example 2

Preparation A

Serum

| Phase | Component | Weight % of total |
| --- | --- | --- |
| A | Propylene glycol | 10 |
| A | Dipropylene glycol | 10 |
| A | Ethanol | 10 |
| A | Ferulic acid | 0.5 |
| A | Baicalin | 0.4 |
| B | Water | 49 |
| B | Vitamin C | 10 |
| B | Caffeine | 5 |
| B | Nicotinamide | 5 |
| B | Baicalin | 0.1 |

Preparation A is made as follows using the above listed components.

The glycol phase (Phase A) components were mixed together at 65° C. except ethanol. After obtained a clear solution and cooled it down to room temperature, ethanol was added. At the same time, the aqueous phase (Phase B) components were mixed at room temperature till clear solution was obtained. The glycol phase was then added into the aqueous phase with constant stirring for another 1 hour and the desired serum was obtained. The final PH was adjusted to 4.5 by using NaOH.

Example 3

Preparation B

Cream

| Phase | Component | Weight % of total |
|---|---|---|
| A1 | Water | 57.5 |
| A1 | Nicotinamide | 5 |
| A1 | Caffeine | 5 |
| A1 | Baicalin | 0.5 |
| A1 | Resveratrol | 0.5 |
| A1 | Ferulic acid | 0.5 |
| A2 | Glycerin | 10 |
| A2 | Xanthan gum | 0.2 |
| A2 | Preservatives | 1 |
| B | Dicaprylyl carbonate | 3 |
| B | Dimethicone | 3 |
| B | Dicapryl alcohol and ceteareth-20 | 4 |
| B | Glyceryl stearate and PEG-100 stearate | 4.5 |
| C | Dimethicone ammonium | 4 |
| C | Polyacryloyldimethyl taurate | 0.3 |
| D | Nylon-12 | 1 |

Preparation B is made as follows using the above listed components.

Phase A1 components were mixed at room temperature in sequence until a clear solution was obtained. In separate containers, Phase A2 was pre-suspended, and then added into Phase A1 with constant stirring and heated to 65° C. At the same time, Phase B components were mixed and completely dissolved at 65° C. Then Phase B was added into Phase A and emulsified for 10-15 minutes. Heating was then stopped, and mixing continued. Phase C was added and mixed for another 10 minutes. After the temperature fell below 40° C. Phase D was added and mix for 10-15 minutes (side sweep) or until powders were fully dispersed, and the desired emulsion was obtained.

What is claimed is:

1. An aqueous cosmetic skin care composition comprising water and
   (a) about 0.1% to about 10% of at least one flavonoid selected from the group consisting of baicalin and taxifolin;
   (b) about 0.1% to about 10% of ferulic acid;
   (c) about 0.1% to about 10% of at least one additional antioxidant selected from the group consisting of Vitamin C and resveratrol; and
   (d) about 0.1% to about 10% of at least one hydrotrope selected from the group consisting of caffeine and nicotinamide, provided that components (a) through (d) are in an amount sufficient to produce synergistic antioxidant activity,
   wherein said skin care composition is appropriate for topical application to the skin and is in the form of a lotion, serum, gel, milk, foam, liquid foundation or cream.

2. The aqueous cosmetic skin care composition of claim 1, wherein said at least one flavonoid (a) is baicalin.

3. The aqueous cosmetic skin care composition of claim 1, wherein said at least one flavonoid is taxifolin.

4. A method for providing antioxidant activity to the skin comprising applying the aqueous cosmetic skin care composition of claim 1 to the skin.

5. The method of claim 4, wherein said at least one flavonoid (a) is baicalin.

6. The method of claim 4, wherein said at least one flavonoid is taxifolin.

* * * * *